United States Patent [19]

Dickakian

[11] Patent Number: 4,781,892

[45] Date of Patent: * Nov. 1, 1988

[54] APPARATUS AND METHOD FOR DETERMINING FOULING TENDENCY OF LIQUID HYDROCARBONS

[75] Inventor: Ghazi B. Dickakian, Kingwood, Tex.

[73] Assignee: Exxon Chemicals Patents Inc., Linden, N.J.

[*] Notice: The portion of the term of this patent subsequent to Nov. 1, 2005 has been disclaimed.

[21] Appl. No.: 910,910

[22] Filed: Sep. 24, 1986

Related U.S. Application Data

[63] Continuation-in-part of Ser. No. 830,386, Feb. 18, 1986, which is a continuation-in-part of Ser. No. 723,598, Apr. 15, 1985.

[51] Int. Cl.[4] .................... G01N 21/17; G01N 30/90; G01N 33/26
[52] U.S. Cl. ........................ 422/69; 73/61.2; 210/198.3; 210/658; 422/68; 436/2; 436/60; 436/162
[58] Field of Search .............. 436/2, 140, 141, 161, 436/162, 60; 73/61.2, 61.1 C, 64, 54; 422/68, 69, 70; 210/658, 198.3

[56] References Cited

U.S. PATENT DOCUMENTS

| | | | |
|---|---|---|---|
| 2,302,224 | 11/1942 | Jones | 73/64 |
| 3,049,964 | 8/1962 | Miller | 356/70 |
| 3,413,842 | 12/1968 | Hecker | 73/61.1 C |
| 3,777,163 | 12/1973 | Aubin et al. | 250/493.1 |
| 3,922,431 | 11/1975 | Radmacher et al. | 73/61.1 C X |
| 3,994,587 | 11/1976 | Yamamoto et al. | 356/73 |
| 4,013,364 | 3/1977 | Nakano et al. | 356/73 |
| 4,145,139 | 3/1979 | Nakamura et al. | 356/73 |
| 4,155,833 | 5/1979 | Gleim | 208/45 |
| 4,544,271 | 10/1985 | Yamamoto | 356/320 |

FOREIGN PATENT DOCUMENTS

| | | | |
|---|---|---|---|
| 0013274 | 6/1968 | Japan | 436/60 |
| 0146040 | 11/1980 | Japan | |
| 0989481 | 1/1983 | U.S.S.R. | |

OTHER PUBLICATIONS

Poirier et al., 1983 Energy Sources, vol. 7, No. 1, pp. 166-176, 1983.

Primary Examiner—Barry S. Richman
Assistant Examiner—Robert J. Hill, Jr.
Attorney, Agent, or Firm—R. L. Graham

[57] ABSTRACT

Apparatus and method for determining the tendency of hydrocarbon liquid to foul equipment includes a horizontal TLC plate, a light source for scanning hydrocarbon liquid sample on the TLC plate, and means for measuring the difference in light reflected by the asphaltene ring and the TLC matrix. Energy sources other than light may be employed.

7 Claims, 2 Drawing Sheets

HIGH-FOULING CRUDE OIL

LOW-FOULING CRUDE OIL

APPARATUS AND METHOD FOR DETERMINING FOULING TENDENCY OF LIQUID HYDROCARBONS

CROSS REFERENCE

This application is a continuation-in-part of U.S. Ser. No. 830,386, filed Feb. 18, 1986, which is a continuation-in-part of U.S. Ser. No. 723,598 filed Apr. 15, 1985.

BACKGROUND OF THE INVENTION

1. Field of the Invention

The present invention relates to an apparatus and method for determining the tendency of liquid hydrocarbon streams to foul equipment and more particularly to an apparatus and method for determining oil-asphaltenes incompatibility and related fouling tendency.

2. Related Art

Petroleum streams, depending on their asphaltene and oil characteristics, have different precipitating and fouling characteristics with regard to heated oil refinery surfaces. The problem of predicting the offending substances in a particular stream such as crude oil which foul heat exchanger equipment in oil refineries and petrochemical plants has been virtually unresolved. Equipment fouling by heated hydrocarbon streams which result in inorganic and carbonaceous deposits on heat exchanger surfaces leads to a blockage of flow and a decrease in heat transfer. Both conditions severely reduce heat efficiency in the processing of the crude oil. A reliable technique for identifying the problem crudes would enable the operator to apply remedial measures such as removing the offending substances or by adding antifouling agents.

There are a number of methods and devices available for determining the rates of fouling of petroleum streams. Conceptually, they are all similar in that they attempt to measure the change in heat transfer from a heated surface to a test fluid. These methods are either not reliable or are time consuming.

One approach is to use a test unit which is designed to allow measurement of the fluid temperature at the exit of the heat-exchanger while the metal temperature of the heated tube is controlled. This configuration provides for close simulation of refinery and petrochemical plant heat-exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature while measuring the change in the liquid outlet temperature. As fouling progresses, i.e., a carbonaceous deposits build up on the heater tube surface, a decrease in the fluid outlet temperature results when using a constant outlet liquid temperature operation. The change in liquid outlet temperature with time provides the basic heat data required for comparative evaluation of untreated material and additive-treated material. The rate of change in outlet liquid temperature versus time shows relative fouling tendencies.

Current test equipment is only capable of measuring the overall tendency of heated petroleum stream to foul refinery equipment and cannot predict which are the offending substances or fractions.

An article entitled "Thin-Layer Chromatographic Method for Determination of Asphaltene Content of Crude Oils and Bitumens", authored by Poirer and George, published in 1983 *Energy Sources,* Volume 7, No. 1, discloses a method which involves determination of asphaltenes content by conventional thin-layer chromatographic (TLC) procedures, extraction of the asphaltenes by toluene, and colorimetric determination of the asphaltenes. This process involves the use of TLC tank with developer solvent. Although described as a fast method, the article states that about 8 hours are required to analyze 15 samples.

Hence, it is an advantage of the present invention that an improved method and apparatus which will rapidly indicate the fouling tendency of asphaltene containing petroleum streams is provided. It is a particular advantage the present invention can be employed in the refinery in a very short period of time by unit operators without extensive chemical training. These and other advantages and features will be apparent from the following test.

SUMMARY OF INVENTION

The method according to one embodiment of the present invention comprises:

(a) depositing a liquid hydrocarbon sample onto a TLC plate, preferably in a horizontal position;

(b) permitting the sample to spread radially thereon whereby the incompatible asphaltenes form a ring on the surface of the TLC plate and the compatible components invade the matrix of the TLC plates;

(c) scanning the spread sample with an energy source (preferably light);

(d) measuring a property (preferably reflected light) which distinguishes the asphaltenes ring from the matrix;

(e) comparing the property of the matrix with that of the asphaltene ring, the value of which provides an indication of the tendency of the liquid hydrocarbon to foul equipment.

The present invention in one aspect also relates to an apparatus which employs thin layer chromatography (TLC) and optics for measuring the tendency of liquid hydrocarbons to foul. The apparatus comprises, in a preferred embodiment:

(a) a TLC plate for receiving a sample of the liquid hydrocarbon on an exposed surface thereof, (b) a light scanner for scanning across the sample received portion of the plate, (c) a light sensor for measuring the light transmitted or reflected by the sample on the plate, and (d) means for comparing the light transmitted or reflected by asphaltenes deposited on the plate with the matrix zone within the sample receiving portion. Matrix refers to the invaded zone without the separated asphaltenes. The matrix may be inside and/or outside the asphaltene ring, depending on the crude oil.

In a preferred embodiment the optical information is converted into a logic level pulse representative of the light reflected. These signals during each scan provide a profile of the liquid hydrocarbon sample. By integrating the area of the profile corresponding to the asphaltene separated portion (matrix profile being 0), the characteristic reading of the samples tendency to foul is obtained. This value can be compared to a standard value of known hydrocarbons.

It has been discovered that the incompatibility of asphaltenes in the liquid hydrocarbon is a measure of the tendency of the liquid to foul. The incompatibility may be detected by the use of thin layer chromatographic (TLC) plates. Depositing a drop of the hydrocarbon stream on the plate produces rings of light (non-fouling) components invaded to the TLC plate matrix and dark (fouling) components precipitated on the TLC plate, usually in the form of a dark ring. These ring formations may be enhanced by the use of diluents, paraffinic solvents, or asphaltene antisolvents such as n-heptane, iso-octane, and decane or solvents containing polar atoms such as alcohols, ketones, amines, ether, etc.

The intensity and area of the asphaltene ring when optically compared to the sample in the TLC plate matrix provides a reliable indication of the fouling tendency of the liquid hydrocarbon. The optical data may be converted to digital output—the value of which classifies a hydrocarbon liquid according to its tendency to foul.

In a preferred embodiment, the method comprises the following steps:

(a) depositing a sample amount (usually one drop) of liquid petroleum from the hydrocarbon stream being monitored onto a flat horizontal surface of a TLC plate which has the property of chromatographic separation of the incompatible asphaltene from the sample by adsorption;

(b) providing sufficient time for radial outward migration of the sample on or in the TLC plate (from about ½ hour to around 2.0 hours) to permit an asphaltene ring to form;

(c) scanning the migrated sample with a light source; and (d) measuring the reflected light throughout the scanned portion.

The difference or ratio of light reflection between the asphaltene ring and the remainder of the sample in the matrix of the TLC plate provides the indication of fouling tendency of the hydrocarbon stream from which the sample was taken.

Once the petroleum stream has been identified as fouling according to the present invention, it can be treated to reduce fouling by incorporating a small quantity of an antifouling agent, such as the well known dispersants used in the refining industry. Thus one aspect of the present invention is a method for reducing the fouling tendency of petroleum streams flowing through a vessel comprising:

DESCRIPTION OF THE PREFERRED EMBODIMENTS OF THE INVENTION

Figure 1:
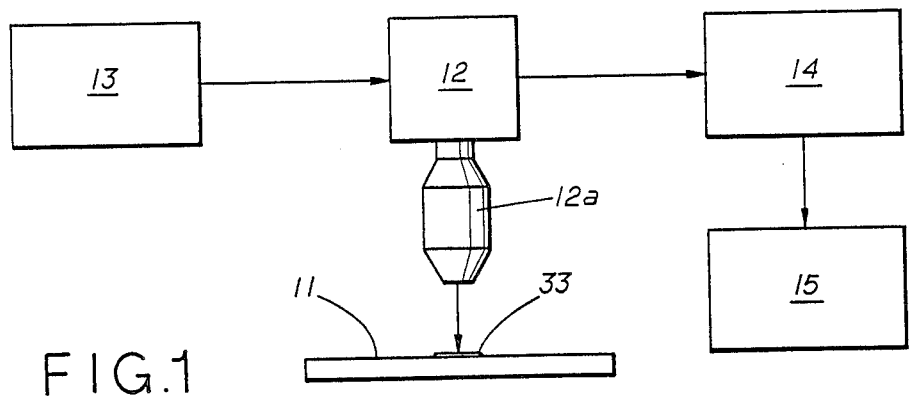
FIG. 1 is a flow diagram schematically illustrated the operation of the apparatus constructed according to the present invention.
Figure 2:
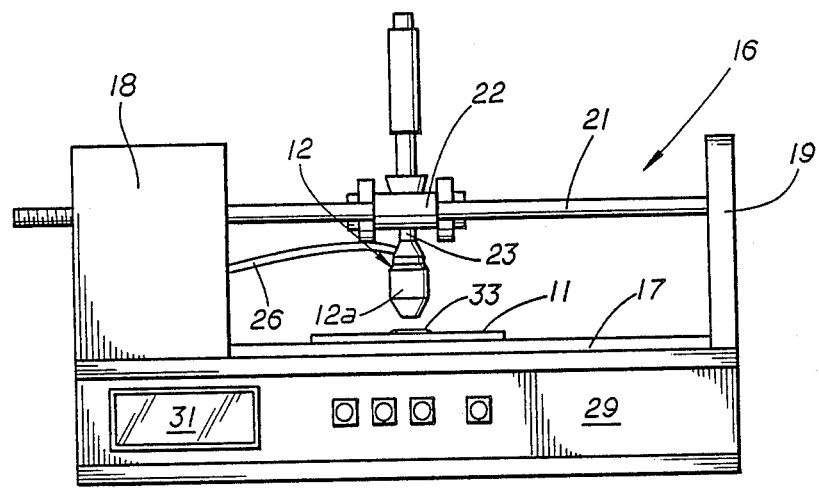
FIG. 2 is a side elevational view of the apparatus constructed according to the present invention.
Figure 3:
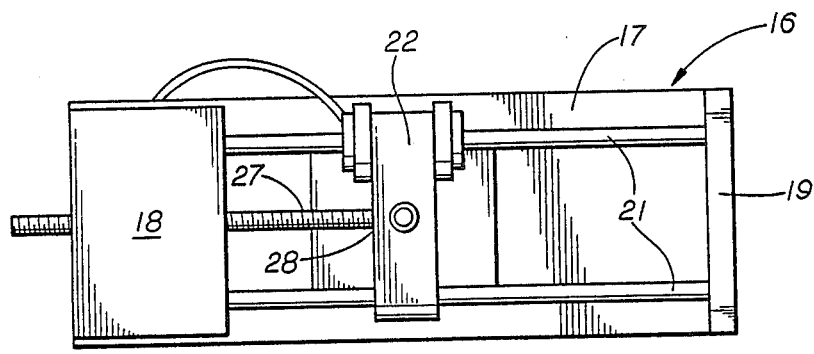
FIG. 3 is a top plan view of the apparatus shown in FIG. 2.

Referring to FIGS. 1, 2, and 3, the apparatus of the present invention comprises a TLC plate 11 for receiving a drop of hydrocarbon liquid, a scanner 12 including light source head 12a and means 13 for moving the scanner 12, means for measuring transmitted or reflective light which may be a part of scanner 12, a data acquisition unit 14 which includes means for comparing transmitted or reflected light in the scanned region and means 15 for converting the data to useful information (e.g. a signal such as a digital signal indicative of the tendency of a liquid hydrocarbon to foul). Optionally, the apparatus may include means for displaying the results.

As shown in FIGS. 2 and 3, the scanner 12, plate 11, and means for moving the light scanner are shown as a single unit 16. The unit 16 comprises briefly a support platform 17, a main housing 18 mounted on one end thereof and an end frame member 19 mounted on the other end thereof. Disposed above the platform 17 and extending in parallel relationship with one another are polished rods 21 which interconnect the main housing 18 and frame member 19. A bar 22 is slideably mounted on the polished rods 21 and provides means for supporting the scanner 12. A vertical rod 23 extends through a central hole of the bar 22 and is secured thereto by set screws (not shown). The scanner 12 is mounted to the lower end of the rod 23. The rod 23 may be provided with telescopically threaded members with micrometer means (not shown) for adjusting the vertical elevation of the scanner 12 in relation to plate 11.

In a preferred embodiment, the scanner 12 comprises a light source and a sensor for measuring the reflected light and converting that into a digital signal which is transmitted to the data acquisition unit 14 by lines 26.

The means for moving the scanner 12 assembly horizontally to scan the sample on the TLC plate 11 is provided by conventional motor and gear assembly. A threaded shaft 27 is mounted by suitable bearings in main housing 18 and has its outer end secured to the bar 22 as at 28. Thus rotation of the shaft 27 through a conventional threaded drive within housing 18 moves the scanner assembly along the polish rods 21. The shaft motor and gear reducers should be designed to provide a relatively slow rectalinear motion. About 2 inches per minute is satisfactory for most applications.

The electronics and circuitry for the instrument including units 14 and 15 may be housed in box 29 underlying support 17. Optionally, the apparatus may include a digital output 31 for indicating the level of the tendency of the sample to foul according to a calibrated scale.

The scanner 12 may be in the form of an industrial digital bar code such as those commercially available from Hewlett Packard with circuitry for converting the reflected optical information to a logic level pulse representative of the reflected light. Alternatively, the scanner 12 may include a separate light source and a high resolution optical reflective sensor, such as Hewlett Packard HEDS-1000. The device includes a light emitter and sensor for sensing the visible light from 600–700 nm.

The pulse signal from the scanner 12 is transmitted to a data acquisition unit such as Hewlett Packard 3421A which converts the pulses into meaningful information that can be represented digitally or graphically by the use of a conventional computer and plotter.

The TLC plate 11 is preferably a high performance silica gel supported on a glass plate. TLC plates 11 which have worked well in the present invention are conventional silica gel plates. These plates have silica gel thickness of about 0.2 mm thickness of silica gel. The size of the plate may vary, but a size of about 10×10 cm or 5×5 cm provides space for many tests. It is believed that asphaltene adsorption plays a major role in the separation of the asphaltene and non-asphaltene, and accordingly finely divided particulate materials which adsorb asphaltenes are preferred TLC plate material.

In practice, the hydrocarbon sample may be used in diluted form (with an asphaltene antisolvent) or undiluted form (neat), on a dry TLC plate, or on a TLC plate wet with the asphaltene antisolvent. A procedure which has provided good results is in accordance with the examples described herein.

In operation, a drop of the liquid hydrocarbon is deposited on a flat surface of a TLC plate. A conventional disposable transfer pipet (Pasteur type 5¾") provides means for depositing drops of substantially the same volume on the plate. After a predetermined period of time in which the sample spreads onto or into the TLC media (usually from 30 minutes to 2 hours), the scanner 12 is passed over the plate scanning the full scope of its radial migration on the plate.

Tests indicate that the nonfouling components including soluble asphaltenes (compatible asphaltenes) invade by capillary action into the TLC plate 11, whereas the incompatible asphaltenes plate out on the surface of the plate 11. Thus the incompatible asphaltenes, being at or near the surface of the plate 11, are effective light absorbers whereas the other components penetrated into the plate 11 and the plate itself reflects light from the light source.

Figure 4:
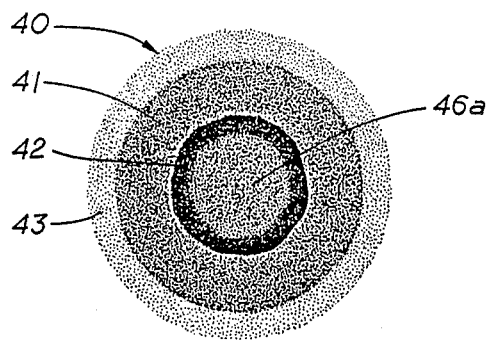
FIG. 4 is an enlarged top plan view of an asphaltene containing hydrocarbon sample after migration on a TLC plate.
Figure 5:
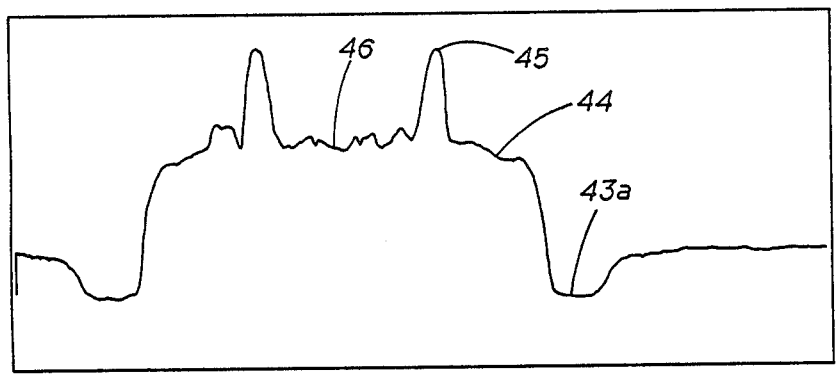
FIGS. 5 and 6 are graphs of a high fouling crude and a low fouling crude, respectively, as measured by the apparatus of the present invention.

The mechanisms involved in distinguishing high fouling crude from low fouling crude will be described with reference to FIGS. 4, 5, and 6. A sample drop 40 as it appears on the TLC plate 11 is illustrated in amplified form in FIG. 4. The drop, after spreading comprises an invaded region indicated at 41 and a dark ring region indicated by ring 42. A light region 43 outside perimeter of region 41 sometimes develops. It is believed that this region consists of very light hydrocarbons which separate from the intermediates. Depending on the amount of incompatible asphaltenes in the sample, the interior 46a of ring 42 may be dark indicating asphaltenes or may be lighter (as illustrated) indicating the same composition of the sample in region 41 outside the asphaltene ring 42. Region 41 and the region 46a are referred to herein as the matrix regions and contain the compatible (nonfouling) components.

The light scanner 12 determines the magnitude of the reflected light in both the matrix regions and the incompatible asphaltene region. The reflected light increases downward and decreases upward as viewed in FIGS. 5 and 6. Viewed another way, absorbed light increases upwardly on the plots of FIGS. 4 and 5. Comparing the plot of FIG. 5 with the sample of FIG. 4, it can be seen that as the scanner 12 moves from right to left, it first encounters a high light reflected area as at 43a which indicates the light hydrocarbon fractions in region 43 of the sample. When the scanner 12 encounters the periphery of region 41 of the sample, the reflected light decreases rapidly to 44 and levels off providing a reading for matrix region 41. Upon encountering the asphaltene ring 42, the reflected light again decreases to 45 and again increases as the scanner 12 enters the central matrix portion 46a. Note that readings of 46 and 44 are approximately the same, indicating the composition in the matrix regions are about the same. Continued movement of the scanner 12 to the left half of the sample provides a generally symmetrical plot of the light reflecting characteristic of the sample on the TLC plate. The key indicator of a crude's tendency to foul is provided by the area of the plot above the base line 44 and 46 (matrix region) which is a function of both the measure of light reflected and the areal extent of ring 42. If this area is large as in FIG. 5, the crude will be found to have a high tendency of fouling. However, if it is small as illustrated in FIG. 6 the tendency to foul will be low. This may be viewed as the volume above the base lines since light reflected is based on the area of the ring and the amplitude of light reflected. In a preferred embodiment the data acquisition unit is programmed to integrate the area above base line 44 and 46 and convert that measurement to a digital reading calibrated according to known fouling tendency.

This reading then can be compared to a standard scale based on crudes of known fouling tendencies. For example, several samples were analyzed by the apparatus of this invention and by the Thermal Fouling Tester (TFT) which is described in Applicant's copending application filed on Apr. 8, 1986 Ser. No. 849,600, the contents of which is incorporated herein by reference.

The following 0-100 scale was developed based on comparing the Apparatus reading and TFT readings.

| Fouling Tendency | Fouling Index of Apparatus | TFT delta T (°F.) |
|---|---|---|
| low | 0-20 | 0-15 |
| medium | 21-40 | 16-39 |
| high | 41-100 | 40+ |

The above scale was developed by calibrating the apparatus with TFT readings based on hundreds of samples.

The present invention thus determines the tendency of hydrocarbon liquids to foul equipment and the results correlate well with the tedious TFT method. Note that the apparatus reading does not correspond to the delta T of the TFT. However, the groupings (high, medium, low) correlated very well.

As used herein, asphaltene incompatibility of the total petroleum stream is indicative of the susceptibility of asphaltenes to separate from the oil, adhere to the heated metal surface, transfer into coke-like material and result in fouling of the metal surface. The greater the incompatibility of the asphaltenes in the oil, the higher the fouling tendency of the hydrocarbon stream.

Asphaltenes present in crude oils have high average molecular weight ($Mn=900-1300$) and a very broad molecular weight distribution. Gel permeation chromatographic (GPC) characterization of two crude oil asphaltenes molecules indicates the presence of molecular weight as high as 5000.

Although best results are generally obtained with diluted samples, in some cases, it may suffice merely to use neat samples.

Paraffinic polar solvents or their blends can be used to dilute the samples and these are effective over a broad range of oil/solvent ratios. Asphaltene is substantially insolvent in these materials. These asphaltene antisolvents must be a low molecular weight, low viscosity and have low boiling characteristics to allow rapid migration on the TLC chromatographic plate.

The paraffin antisolvents are preferably up to $C_{18}$ straight or branched alkanes. Usually $C_5$ to $C_{10}$, e.g., suitable antisolvents include pentane, isopentane, hexane, 2-methyl hexane, n-heptane, octane, nonane, decane, isooctane and the like.

The polar antisolvents cover a broader spectrum of materials. The present polar solvents are organic compounds which are liquids under the conditions of use. The term "polar" refers to atoms such as oxygen, sulfur, oxygen, halogens and nitrogen. A partial listing of suitable polar antisolvents includes alcohols such as, isobutanol, 2-pentanol, isoamyl alcohol; ketones such as acetone; methyl ethyl ketone; ethers such as diethyl ether, methyl propyl ether; esters such as methyl formate, butyl formate, methyl acetate, methyl propionate; glycol ethers, such as ethylene glycol monomethyl ether, ethylene glycol diethyl ether; heteroatom compounds such as furan, tetrahydrofuran, furfural, methyl pyridine, and the like. Mixtures of hydrocarbon and polar materials are desired antisolvents for petroleum streams containing functional groups. The selection of a suitable antisolvent depends on the atmospheric temperature of the TLC plate. For example, in the laboratory (20° C.) n-heptane or n-decane were used satisfactorily. On-site testing in cold weather, may require pentane or isoctane, whereas a refinery site in hot weather such as in Texas or Louisiana where the TLC glass plate will have high temperature, may require a high boiling antisolvent such as nonane or decane.

The present invention of fouling characterization is simple and easy to use in the laboratory and in the field for monitoring crude oil characteristics routinely by non-technical personnel. The method may be used in three ways: (a) use of antisolvent in the oil sample, (b) use of antisolvent on the TLC plate, and (c) use of neat sample. The use of antisolvent is preferred however since it appears to be the most versatile in the variety of crudes capable of testing.

(a) As described above, the antisolvent can be added to and blended with the crude oil. The blend (one drop) then is deposited on the TLC plate. The spreading of the sample to form a circular invaded zone will develop in a very short time. The sample is then scanned and the reflected light measured as described previously. FIGS. 5 and 6 are representative of the instrument output plot.

The ratio of antisolvent to oil will obviously vary from crude to crude, not only for the enhancement of the insolubility of the asphaltenes but also to reduce the viscosity of the crude to an extent to make it operable with the TLC chromatographic plate. Light and medium crudes require only a few minutes for development of the chromatographic pattern, whereas heavy crudes, such as the California crudes, may require a few hours.

The antisolvent is preferably added to the oil in a ratio ranging from 0.2:1 to 1:0.2, more preferably 0.5:1 to 1:0.5 (antisolvent:oil ratio). The use of the correct oil/antisolvent ratio is important for the successful separation of asphaltene and oil on the TLC plate. When adding the antisolvent to the oil, the antisolvent will insolubilize the asphaltene, especially the low molecular weight part of the asphaltenes and produce a very clear and well defined asphaltene ring on the TLC plate, which can then be easily related to fouling characteristics with greater assurance by the unit operator using the test. The preferred antisolvents include $C_5$-$C_{10}$ hydrocarbons straight and branched al-kanes at a ratio wherein the hydrocarbon liquid comprises the major volume proportion. The preferred system comprises from 10 to 30 volume percent of pentane, isopentane, hexane, 2 methyl hexane, n-heptane, octane, nonane, decane, isoctane, or mixtures of these and 70 and 90 volume percent of the liquid hydrocarbon.

(b) The present method can also be used by simply adding one or a few drops of the antisolvent onto the dry TLC plate (just to wet the thin film) and then applying a drop of the oil onto the wet film and allowing the chromatogram to develop followed by scanning as described above. This method is particularly suitable for on-site tests in the refinery. It is also possible to use a combination of the two embodiments of the present invention, which may be useful with very heavy crudes.

(c) The neat crude oil sample may be deposited directly on the TLC plate, followed by the steps described above.

The following procedure was used in Examples I, II, and III to produce the several thin layer chromatograms:

EXPERIMENTS

The following two forms of the apparatus was used, both employing reflected light as the operative mechanism:

(1)
  TLC plate:
    Silica gel 60 TLC plate supplied by E. Merck, Darmstate, Germany
  Scanner:
    Hewlett Packard Optical Reflective Sensor Model HEDS-1000
  Data Acquisition:
    Hewlett Packard 3421A
  Unit Plotter:
    by Hewlett Packard UX Integral Personal Computer of Hewlett Packard programed for graphics.

(2) A second unit was provided with the same TLC plate and scanner. Instead of the plotter, a computer capable of integrating the area above the matrix reading was built into the apparatus and provided only with digital output of the fouling index based on the scale described above.

EXAMPLE 1

A drop of a high fouling crude oil (as determined by TFT) with antisolvent (1 part volume decane plus 4 parts crude) was placed on the TLC plate (dry) and permitted to migrate for 60 minutes at room temperature. The TLC plate sample then was scanned with instrument (1) above and the graph shown in FIG. 5 was produced. Note that the plot of FIG. 5 corresponds to the sample of FIG. 4 previously described. The fouling index as read by the Apparatus was 90, indicating a high fouling crude.

EXAMPLE 2

Figure 6:
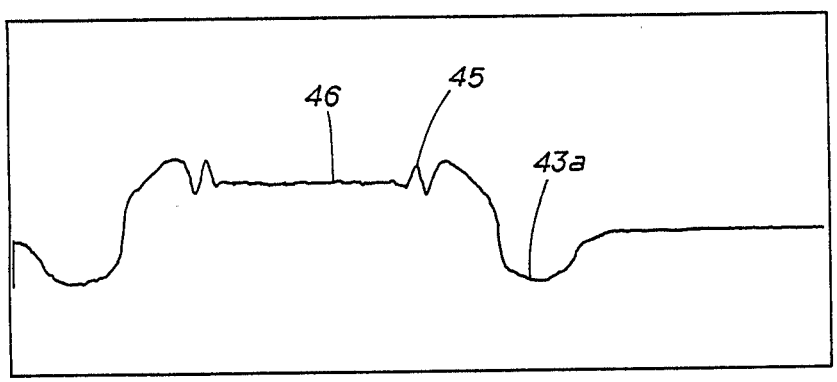

The same test was run using a low fouling crude (as determined by TFT) which gave the plot of FIG. 6. This sample gave a fouling index reading of 5 by Apparatus 1, indicating a low fouling crude.

EXAMPLES 3-11

Additional samples with 20 volume % of decane were analyzed using the same procedures as described in Example 1 except that apparatus (2) was employed which provided a digital reading based on the above fouling index scale. The fouling index and corresponding TFT reading are presented in the Table.

TABLE

| Example | Apparatus Fouling | | TFT Fouling | |
|---|---|---|---|---|
| | Fouling Index | Fouling Tendency | T (°F.) | Fouling Tendency |
| 3 | 0 | Low | 0 | Low |
| 4 | 10 | Low | 2 | Low |
| 5 | 7 | Low | 0 | Low |
| 6 | 24 | Medium | 36 | Medium |
| 7 | 25 | Medium | 23 | Medium |
| 8 | 22 | Medium | 18 | Medium |
| 9 | 46 | High | 126 | High |
| 10 | 66 | High | 105 | High |
| 11 | 86 | High | 132 | High |

Although the present invention has been described with emphasis on reflective light as the operative mechanism, it will be apparent that other energy sources and measurements of parameters or properties responsive thereto may be employed as the means for distinguishing asphaltenes on the TLC plate and determining the ratio of the responsive parameter with the matrix. These include transmitted light, audio waves, x-rays, ultrasonic, ultraviolet and the like.

What is claimed is:

1. An apparatus for measuring the tendency of a hydrocarbon liquid to foul equipment which comprises:
    (a) a thin layer chromatographic plate for receiving a sample of a hydrocarbon liquid on an internal portion thereof, said plate being capable of separating incompatible asphaltenes from compatible components of a sample of a hydrocarbon liquid to form an incompatible asphaltene ring region and a matrix region of compatible sample components on or in the internal portion of said plate;
    (b) a light source adapted to scan the internal portion of the plate;
    (c) means for measuring light from the light source which has been affected by the internal portion of the plate;
    (d) means for comparing measured light corresponding to an asphaltene ring region of the internal portion of the plate with measured light corresponding to a matrix region of the internal portion of the plate and generating a corresponding comparison signal; and
    (e) means for receiving a comparison signal from the comparing means and converting such a comparison signal into an electric signal indicative of the tendency of a liquid hydrocarbon to foul equipment.

2. An apparatus for measuring the tendency of a hydrocarbon liquid to foul equipment which comprises:
    (a) a substantially horizontal thin layer chromatographic plate for receiving a sample of a hydrocarbon liquid on an internal portion thereof, said plate being capable of separating incompatible asphaltenes from compatible components of a sample of a hydrocarbon liquid to form an incompatible asphaltene ring region and a matrix region of compatible sample components on or in the internal portion of said plate;
    (b) a light source adapted to scan the internal portion of the plate;
    (c) means for measuring light from the light source which is transmitted through or reflected by the internal portion of the polymeric plate;
    (d) means for comparing light transmitted through or reflected by an asphaltene ring region of the internal portion of the plate with light transmitted through or reflected by a matrix region of the internal portion of the plate and generating a corresponding comparison signal; and
    (e) means for receiving a comparison signal from the comparing means and converting such a comparison signal into an output signal indicative of the tendency of a liquid hydrocarbon to foul equipment.

3. The apparatus of claim 2 wherein the output signal is a digital signal.

4. The apparatus as defined in claim 2, wherein the comparing means includes means for measuring (i) the area and intensity of light reflected by an asphaltene ring region of the internal portion of the plate and (ii) the area and intensity of light reflected by a matrix region of the internal portion of the plate.

5. The apparatus of claim 2 wherein the means for measuring light comprises means for measuring reflected light; and the comparison means comprises means for comparing reflected light from an asphaltene ring region of the internal portion of the plate with reflected light from a matrix region of the internal portion of the plate.

6. The apparatus of claim 5 wherein the means for measuring reflected light includes a light sensor for measuring light reflected from the internal portion of the plate through one pass of the light source over the internal portion of the plate and means for converting measured reflected light into electric signals, and wherein the comparison means includes means for comparing electric signals corresponding to an asphaltene ring region of the internal portion of the plate with electric signals corresponding to a matrix region of the internal portion of the plate.

7. The apparatus of claim 6 wherein the comparison means includes means for comparing (i) the average value of electric signals corresponding to an asphaltene ring region of the internal portion of the plate multiplied by the area of such an asphaltene ring region with (ii) the average value of electric signals corresponding to a matrix region of the internal portion of the plate multiplied by the area of such a matrix region.

* * * * *